United States Patent
Allison et al.

(10) Patent No.: US 7,019,184 B2
(45) Date of Patent: Mar. 28, 2006

(54) NON-OXIDATIVE CONVERSION OF GAS TO LIQUIDS

(75) Inventors: Joe D. Allison, Ponca City, OK (US); Neil Meldrum, Houston, TX (US); Doug S. Jack, Ponca City, OK (US); Marc J. Ledoux, Strasbourg (FR)

(73) Assignee: Conocophillips Company, Houston, TX (US)

( * ) Notice: Subject to any disclaimer, the term of this patent is extended or adjusted under 35 U.S.C. 154(b) by 323 days.

(21) Appl. No.: 10/139,502

(22) Filed: May 6, 2002

(65) Prior Publication Data

US 2003/0144565 A1 Jul. 31, 2003

Related U.S. Application Data

(60) Provisional application No. 60/352,445, filed on Jan. 28, 2002.

(51) Int. Cl.
C07C 15/00 (2006.01)
C07C 2/52 (2006.01)
C07C 6/00 (2006.01)
C07C 5/067 (2006.01)

(52) U.S. Cl. ............ 585/415; 585/407; 585/418; 585/420; 585/424; 585/446; 585/448; 585/470; 585/943

(58) Field of Classification Search ............ 585/407, 585/415, 418, 420, 424, 446, 448, 470, 943
See application file for complete search history.

(56) References Cited

U.S. PATENT DOCUMENTS

| 4,952,547 A | 8/1990 | Annapragada et al. ...... 502/213 |
| 5,635,541 A | 6/1997 | Smith et al. ............. 518/703 |
| 5,936,135 A | 8/1999 | Choudhary et al. ......... 585/418 |
| 5,950,732 A | 9/1999 | Agee et al. .............. 166/354 |
| 6,005,011 A | 12/1999 | Henningsen .............. 518/706 |
| 6,117,916 A | 9/2000 | Allam et al. ............. 518/702 |
| 6,225,358 B1 | 5/2001 | Kennedy ................. 518/700 |
| 6,262,131 B1 | 7/2001 | Arcuri et al. ............ 518/700 |
| 6,277,894 B1 | 8/2001 | Agee et al. .............. 518/700 |
| 6,342,316 B1 * | 1/2002 | Okamoto et al. ............ 429/19 |
| 2002/0072642 A1 | 6/2002 | Allison et al. ............ 585/418 |

OTHER PUBLICATIONS

PCT International Search Report for International Application NO. dated Mar. 23, 2003 (3 p.).
[Online]. Retrieved from the Internet Jan. 16, 2002: <URL:http://www.fisher–tropsch.org/DOE/DOE_reports/de98054194/de98054194_toc.htm.
[Online]. Retrieved from the Internet Jan. 16, 2002: URL:http://www.natl.doe.gov/publications/proceedings/97/97ng/no97-pdf/Nap15.pdf.
[Online]. Retrieved from the Internet Jan. 16, 2002: URL:http://www.ipt.unit.no/~ngh/library/paper11/Amsterdam2001Stranded.htm.
[Online]. Retrieved from the Internet Jan. 16, 2002: URL:http://www.ipt.ntnu.no/~ngh/library/paper5/paper5.html.

* cited by examiner

*Primary Examiner*—Tam Nguyen
(74) *Attorney, Agent, or Firm*—Conley Rose; Kim S. Manson (57) ABSTRACT

The present invention provides a process for natural gas in the form, e.g., of stranded gas or associated gas to transportable liquids. More particularly, the present invention provides a process in which the gas is non-oxidatively converted to aromatic liquid, preferably in proximity to the wellhead, which may be onshore or offshore. In one aspect, the present invention provides integration of separation of wellhead fluids into associated gas and crude with blending of the aromatic liquid derived from the gas with the crude. Alternatively, or in combination, in another aspect, the present invention provides integration of conversion of byproduct hydrogen to power with non-oxidative conversion of gas to aromatic liquid.

38 Claims, 4 Drawing Sheets

NON-OXIDATIVE CONVERSION OF GAS TO LIQUIDS

CROSS-REFERENCE TO RELATED APPLICATIONS

The present application claims the benefit of priority from U.S. Provisional Application Ser. No. 60/352,445, filed Jan. 28, 2002, entitled "Non-Oxidative Conversion of Gas to Liquids Offshore". Further, the present application is related to U.S. application Ser. No. 09/916,469, filed Jul. 27, 2001, which claims the benefit of priority from U.S. Provisional Application Ser. No. 60/221,082, filed on Jul. 27, 2000, each entitled "Catalyst and Process for Aromatic Hydrocarbons Production from Methane". Still further, the present application is related to U.S. application Ser. No. 10/139,485, concurrently filed, which claims the benefit of priority from U.S. Provisional Application 60/299,545, filed May 6, 2002, each entitled "Circulating Catalyst System and Method for Conversion of Light Hydrocarbons to Aromatics". Each of the above-listed applications is hereby incorporated herein by reference.

STATEMENT REGARDING FEDERALLY SPONSORED RESEARCH OR DEVELOPMENT

Not Applicable.

FIELD OF THE INVENTION

The present invention relates generally to a process for natural gas in the form, e.g., of stranded gas or associated gas to transportable liquid. More particularly, the present invention relates to a process in which the gas is non-oxidatively converted to aromatic liquid, preferably offshore in proximity to the wellhead.

BACKGROUND OF THE INVENTION

There has been recognition in the prior art that it is desirable to convert methane into a higher molecular weight hydrocarbon. For instance, it is known that it is normally commercially unfeasible to transport methane produced with crude oil or natural gas from a well site to a distant location for consumption as fuel. Often the transportation problems relate to the extremely low temperatures needed to liquefy methane or to liquefy a gas mixture containing large amounts of methane.

The composition of natural gas at the wellhead varies, but the major hydrocarbon present is methane. For example, the methane content of natural gas may vary within the range of from about 40 to 95 volume percent. Other constituents of natural gas may include ethane, propane, butanes, pentanes (and heavier hydrocarbons), hydrogen sulfide, carbon dioxide, helium and nitrogen. Conventional processing of wellhead natural gas yields processed natural gas containing at least a major amount of methane.

It is normally very costly to separate other light hydrocarbons such as ethane from methane and it is undesirable to mix methane with other hydrocarbons prior to transport. The result has been that large amounts of methane are essentially disposed of in a wasteful manner as by flaring without utilization of the hydrocarbonaceous nature of the methane.

Thus there has been interest in developing processes for the conversion of gaseous fuels, including natural gas and methane, to easily transportable, less volatile, value-added products, methanol and syncrude. Syncrude is synthetic crude produced by first converting methane to a mixture of carbon monoxide and hydrogen, termed synthesis gas, followed by conversion of the synthesis gas via the Fischer-Tropsch reaction to paraffinic hydrocarbons.

A. H. Singleton, et al. in an article entitled "Conversion of Associated Natural Gas to Liquid Hydrocarbons", in the Proceedings of the Natural Gas Conference, Emerging Technologies for the Natural Gas Industry, 1997, available for download at http://www.doe.gov/publications/proceedings/97/97 ng/ng97_pdf/NGP15.PDF on or before Jan. 16, 2002, describes a plant and process for converting associated gas to syncrude on a FPSO (Floating Production, Storage, Off-loading vessel) off-shore and mixing the syncrude with crude oil separated from the associated gas. The process includes steam reforming of methane to oxidatively produce synthesis gas followed by Fischer-Tropsch catalytic reaction of the synthesis gas to produce paraffinic hydrocarbons. This process has the disadvantage of requiring intermediate production of synthesis gas. Thus, it is an indirect process.

U.S. Pat. No. 6,005,011, issued to G. Henningsen, describes a plant and process for converting associated gas from crude oil to methanol at or near the wellhead. The process uses partial oxidation of the associated gas. Thus, the process has the disadvantage of requiring a source of oxygen.

U.S. Pat. No. 5,635,541, issued to A. R. Smith et al., and U.S. Pat. No. 6,117,916, issued to R. J. Allam, et al. each describe air separation units for generation of oxygen for partial oxidation of remote natural gas. These patents teach that operation of an air separation unit tend to require power to supply the thermodynamic work of air compression. Thus, use of air separation units has the disadvantage of tending to make demands of power.

Notwithstanding the above teachings, there remains a need for an economical non-oxidative direct process for conversion of natural gas to transportable liquids at the wellhead.

SUMMARY OF THE PREFERRED EMBODIMENTS

According to a preferred embodiment of the present invention, a process for converting a gaseous hydrocarbon stream to an aromatic hydrocarbon stream features passing the gaseous stream from a wellhead to a non-oxidative conversion zone proximous to the wellhead and contacting the gaseous stream with a catalyst contained in the conversion zone so as to produce the aromatic liquid stream.

The aromatic liquid stream is preferably produced directly from the gaseous stream without intermediate reaction.

The gaseous stream preferably includes at least 40 volume % methane, more preferably at least 50 volume % methane. The aromatic stream preferably includes aromatic hydrocarbons selected from the group consisting of benzene, xylenes, and naphthalene.

According to an alternative preferred embodiment of the present invention, a process for converting wellhead fluids to blended crude features separating the fluids into associated gas and crude oil, passing a methane-containing feed stream derived from the associated gas to a non-oxidative conversion zone so as to produce aromatic liquid, and blending the aromatic liquid with the crude oil so as to produce the blended crude.

In any of the above-described embodiments, the conversion zone may be located onshore. Alternatively, the conversion zone may be located an offshore facility. The facility may be a fixed platform. Alternatively, the facility may be a floating structure, such as an FPSO.

In any of the above-described embodiments, the process may further include passing byproduct hydrogen produced from contact of the gaseous stream with the catalyst to a power generation unit. The power generation unit may be a fuel cell. Alternatively, the power generation unit may be a combustion chamber for combustion of hydrogen. The process may still further include passing power from the power generation unit to a power consuming unit. The power consuming unit may be the conversion zone. Alternatively, the power consuming unit may be the above-described facility bearing the conversion zone. Thus, the power consuming unit may be a floating structure. Still alternatively, the power consuming unit may be any suitable system located on or within the facility bearing the conversion zone.

The process may further include processing the associated gas to produce the methane-containing feed stream. The feed stream preferably includes at least 40 volume % methane, more preferably at least 50 volume % methane. The aromatic liquid may include aromatic hydrocarbons selected from the group consisting of benzene, xylenes, and naphthalene.

An advantage of the above-described processes is the absence of the use of oxygen in the conversion of gas to transportable liquid. Thus, the process has improved economics and safety.

Further, another advantage is the power savings introduced in embodiments including utilizing byproduct hydrogen to power the non-oxidative conversion.

Still further, another advantage is the economy of transport introduced in embodiments including blending aromatic liquid derived from associated gas with the crude separated from the associated gas for transportation as one liquid, in particular blended crude. The blended crude may be transported by a pipeline. Alternatively, the blended crude may be transported by a shuttle tanker.

Thus, the preferred embodiments of the present invention comprises a combination of features and advantages which enable it to overcome various problems of prior methods. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiments of the present invention, reference will now be made to the accompanying drawings, in which like reference numbers indicate like features, wherein.

DETAILED DESCRIPTION OF THE PREFERRED EMBODIMENTS

Process for Converting Gas to Liquids

Figure 1:
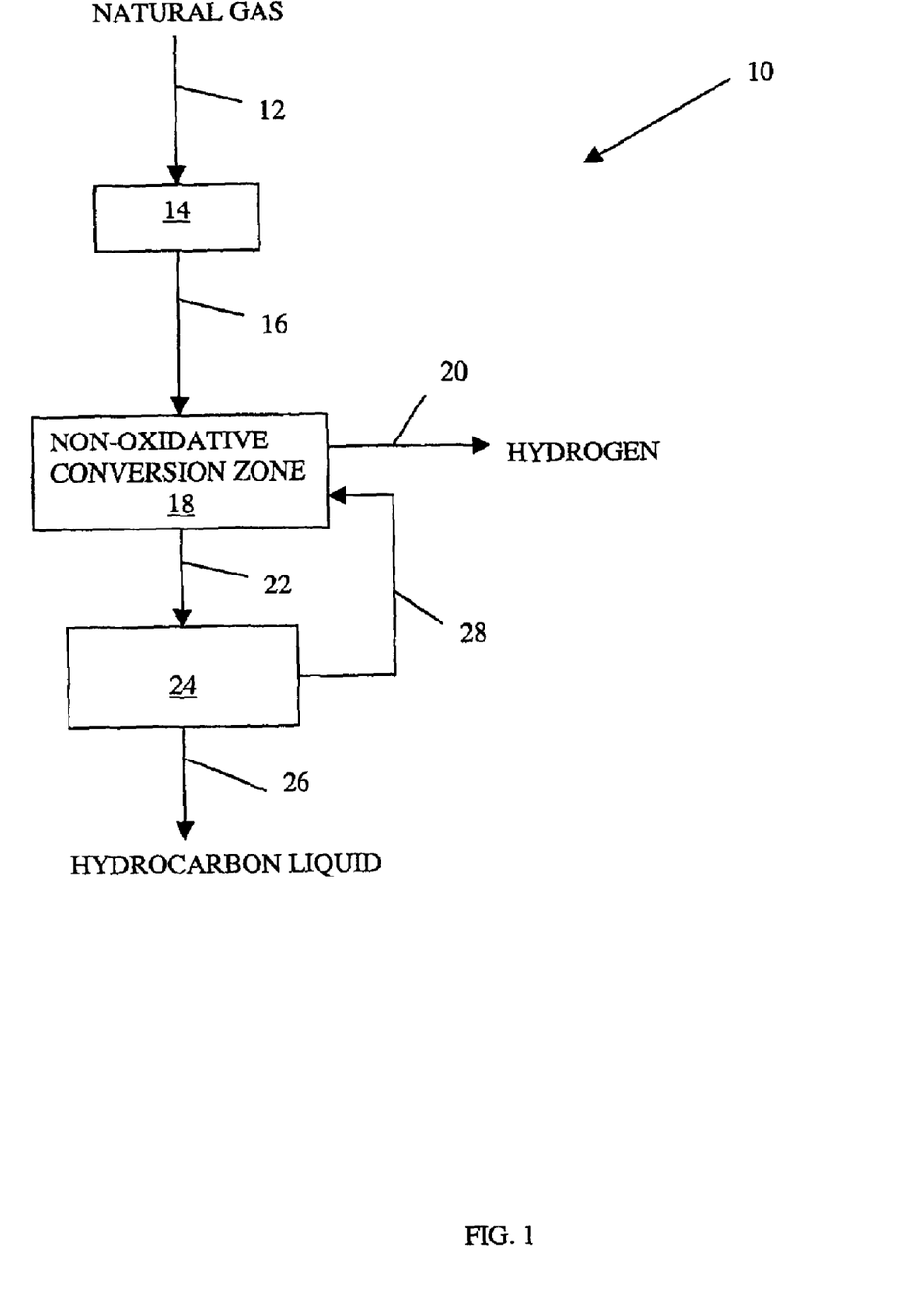
FIG. 1 is a schematic representation of a gas to aromatics process according to a preferred embodiment.

Referring now to FIG. 1, according to a preferred embodiment, a system 10 for converting natural gas 12 to aromatic liquid 26 includes a processing unit 14, a non-oxidative conversion unit 18, and a product separation unit 24. Natural gas 12 is supplied to processing unit 14, where it is processed to produce feed stream 16. Feed stream 16 is supplied to non-oxidative conversion zone 18, where feed stream 16 is contact with a catalyst so as to produce product stream 22 and byproduct hydrogen stream 20. According to some embodiments hydrogen stream 20 is flared. Product stream 22 is supplied to product separation unit 24, where product stream 22 is separated into aromatic liquid 26 and any unreacted gas 28. Gas 28 is preferably recycled to conversion zone 18. Aromatic liquid contains 26 one or more aromatic hydrocarbons liquid under standard conditions.

Figure 2:
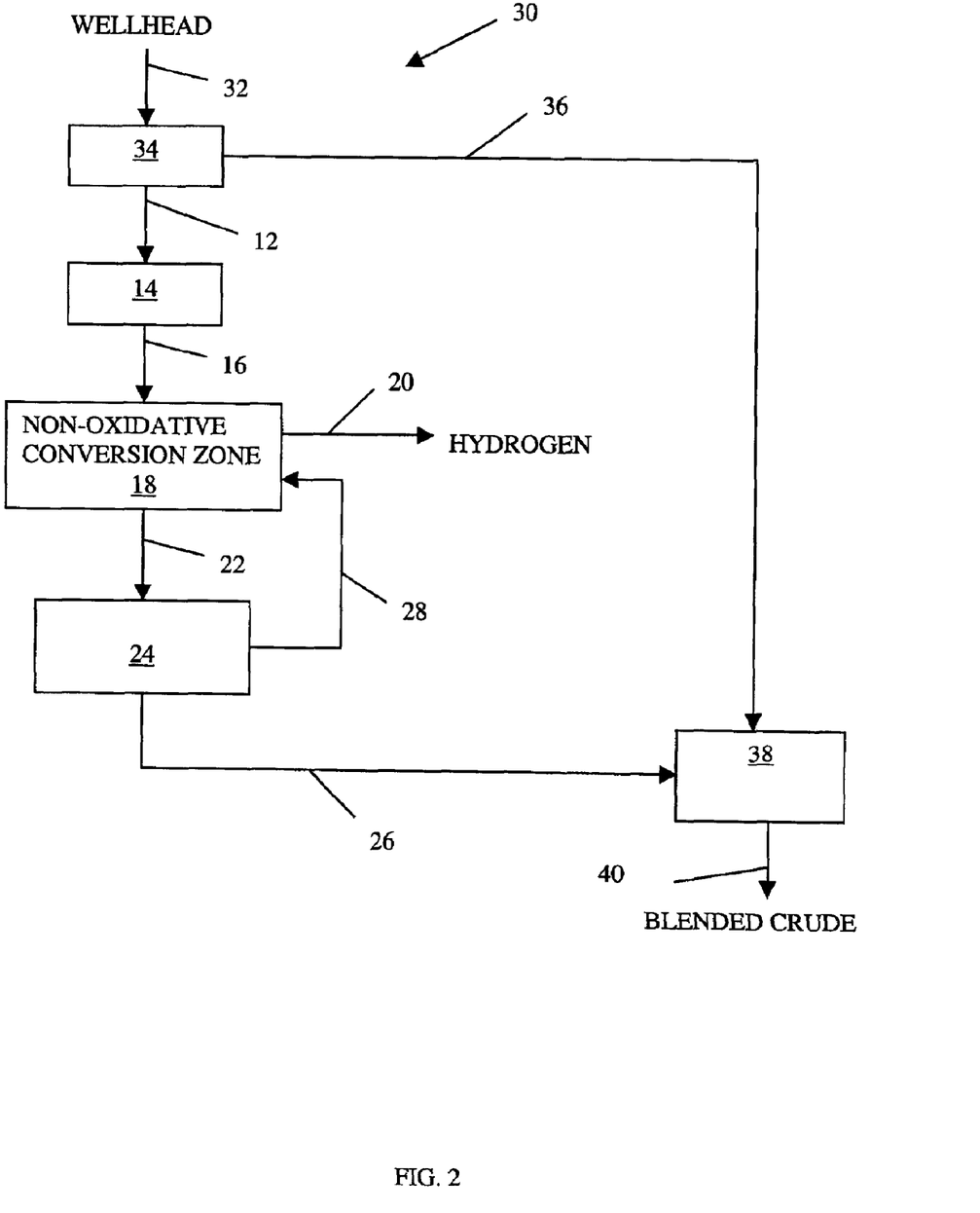
FIG. 2 is a schematic representation of integration of the process of FIG. 1 with separation of wellhead fluids into crude and associated gas and blending of the aromatics produced from the gas with the crude.

Referring now to FIG. 2, according to an alternative preferred embodiment, a system 30 includes system 10 and further includes a fluids separation unit 34 and a blending unit 38. Fluids 32 from a wellhead are supplied to fluids separation unit 34, where fluids 32 are separated into natural gas 12, as associated gas, and crude oil 36. Crude 36 is supplied to blending unit 38. Further, aromatic liquid 26 is supplied to blending unit 38. Aromatic liquid 26 is blended with crude 36 in blending unit 38 so as to produce blended crude 40. Blended crude 40 may then be transported in a conventional oil pipeline or conventional shuttle tanker.

Figure 3:
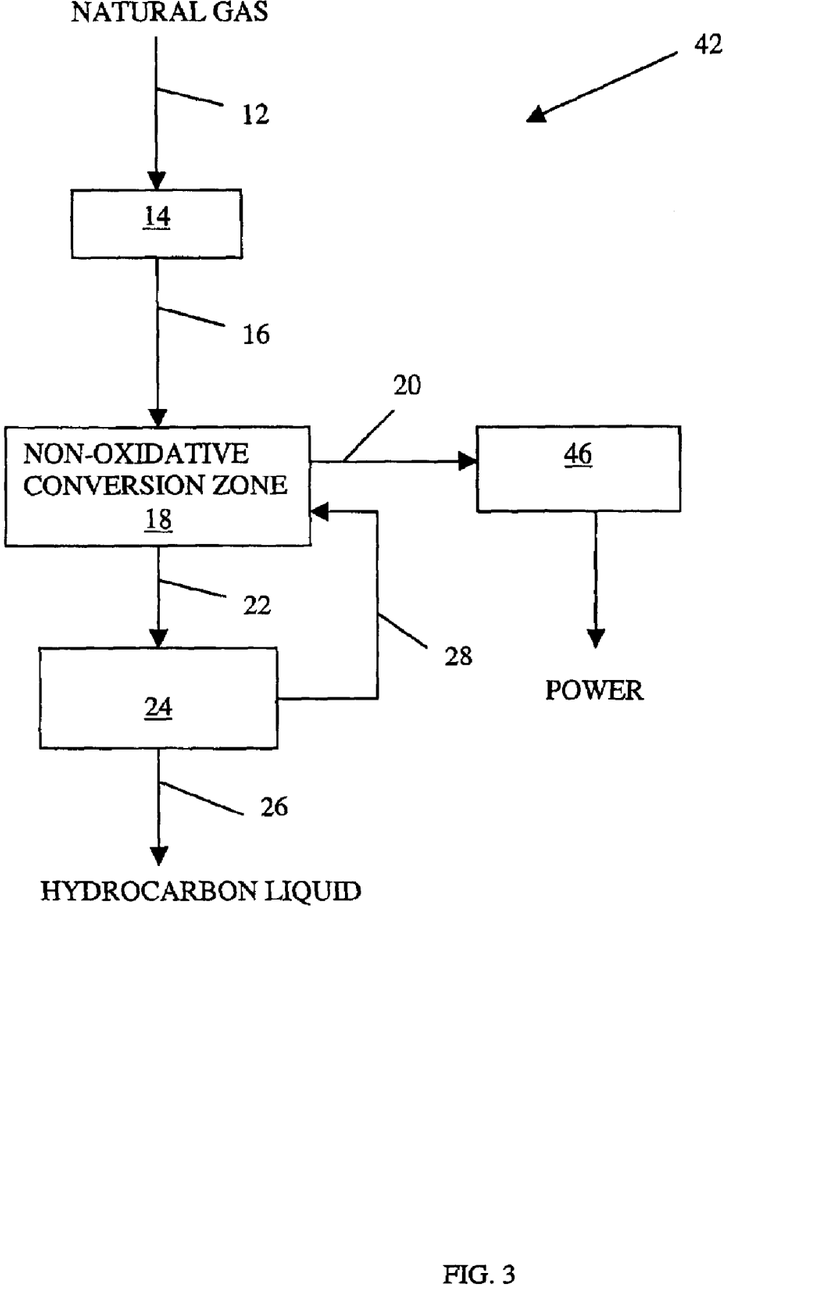
FIG. 3 is a schematic representation of integration of the use of byproduct hydrogen for power generation with the process of FIG. 1.
Figure 4:
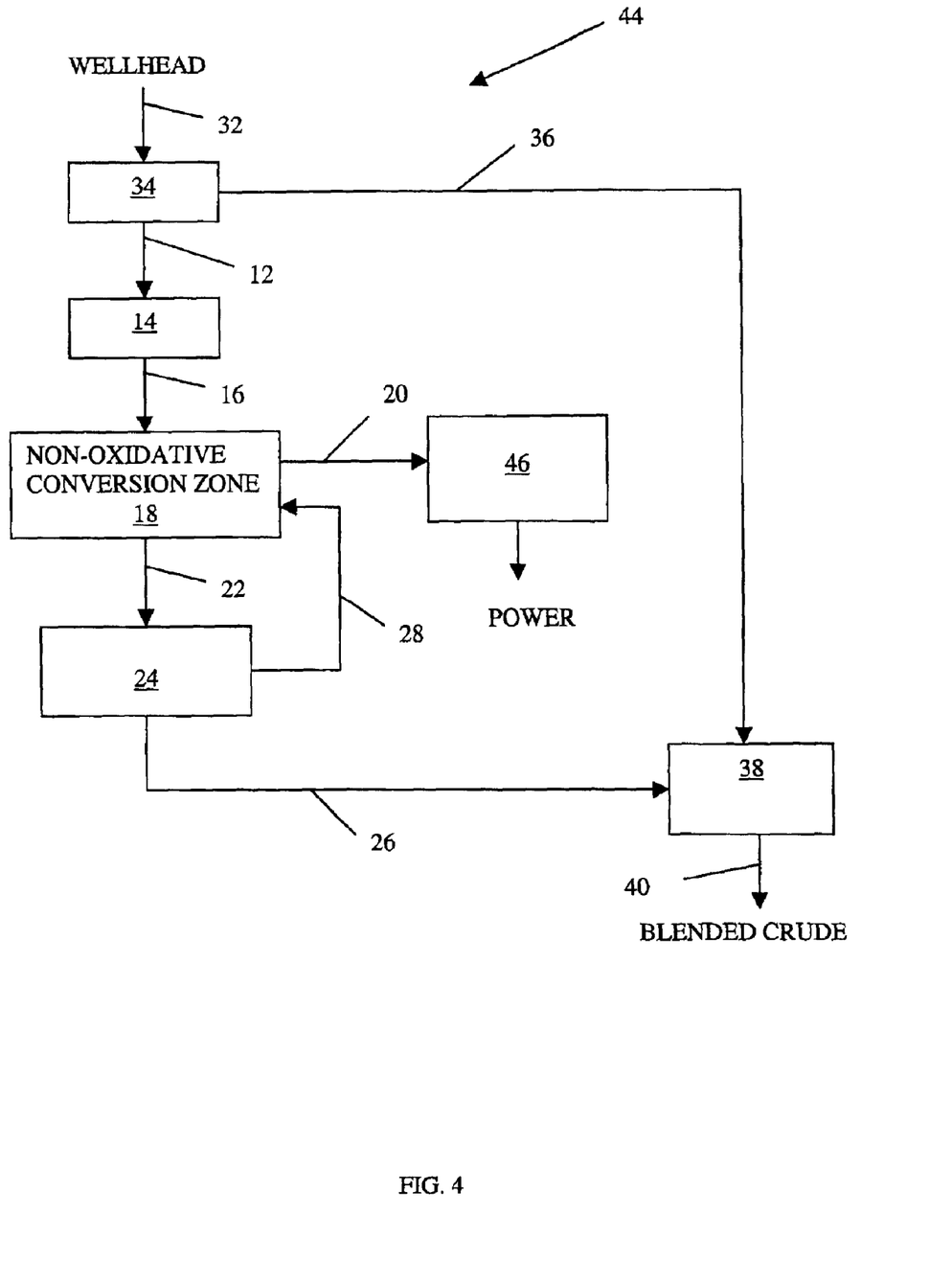
FIG. 4 is a schematic representation of integration of the use of byproduct hydrogen for power generation with the process of FIG. 1.

Referring now to FIGS. 3 and 4, according to yet alternative preferred embodiments, systems 42, 44, respectively, include systems 10 and 30, respectively, and further include a fuel cell 46. Hydrogen 20 is supplied to power generation unit 46. Power generation unit 46 generates power. The power preferably is supplied to the conversion unit 18. Power generation unit 46 may be a fuel cell. Alternatively, power generation unit 46 may be a combustion chamber for combustion of hydrogen. The process may still further include passing power from the power generation unit to a power consuming unit. The power consuming unit may be the conversion zone. Alternatively, the power consuming unit may be a facility bearing the conversion zone. Thus, the power consuming unit may be an FPSO. Alternatively, the power consuming unit may be an off-shore platform. Still alternatively, the power consuming unit may be any suitable system located on or within the facility bearing the conversion zone. Yet alternatively, the power consuming unit may be a nearby facility or system located thereon.

In a preferred arrangement, any one of systems 10, 30, 42, 44 is located at the source of natural gas 12. For example, any one of systems 10, 30, 42, 44 may be located offshore. According to one embodiment, any one of systems 10, 30, 42, 44 is mounted on an offshore platform. The offshore platform conventionally remains in a fixed location. Alternatively, any one of systems 10, 30, 42, 44 is mounted on a floating structure. The floating structure may be a FPSO (Floating Production, Storage, Off-loading vessel.) The FPSO is conventionally based on a converted surplus tanker and can be moved from one location to another. The footprint of any one of systems 10, 30, 42, 44 is preferably smaller than the footprint of a conventional plant for dehydrating natural gas for export. Alternatively, or in combination, the footprint of any one of systems 10, 30, 42, 44 is smaller than the footprint of a conventional plant for processing natural gas for injection. Thus, any one of systems 10, 30, 42, 44 preferably is adapted to be installed as a retrofit on an existing fixed platform or floating structure. Alternatively, any one of systems 10, 30, 42, 44 may be located on land.

Referring to FIGS. 1–4, according to a preferred embodiment, natural gas 12 is obtained from a well from which it is uneconomical to transport natural gas via a pipeline. Thus, natural gas 12 may be any one or combination of stranded gas, associated gas, compressed gas, and the like. Natural gas 12 is preferably produced from a well at a rate of between about 50 thousand and about 200 million standard cubic feet per day. Preferably between about 10 and 10,000 barrels per day of aromatic liquid 26 is produced.

Still referring to FIGS. 1–4, processing unit 14 preferably converts natural gas 12 into a suitable feed stream 16 for non-oxidative conversion unit 18. Natural gas 12, when derived from a typical reservoir, may contain light hydrocarbons, such as methane, ethane, propane, butanes, and propanes. Natural gas 12, when derived from a typical reservoir, may contain non-hydrocarbon compounds such as carbon dioxide, helium, hydrogen sulfide, and nitrogen. Process unit 14 may include one or more conventional subunits for separating any one or combination of the above-listed non-methane components of natural gas from the methane.

Still referring to FIGS. 1–4, further description of feed stream 16, non-oxidative conversion zone 18, and product stream 22 is contained below in the section entitled "Non-oxidative conversion process".

Referring still to FIGS. 1–4, product separation unit 24 contains at least one separator that separates gases from liquids. Such separators are well known to one of ordinary skill in the art. The gases are passed to gas stream 28. The liquids are passed to aromatic liquid stream 26. Gas stream 28 is preferably recycled to non-oxidative conversion zone 18. Alternatively, gas stream 28 may be used to drive a gas turbine for power generation. Still alternatively, gas stream 28 may be flared if the content of gas stream 28 is suitable for flaring.

Referring now to FIGS. 2 and 4, fluids separation unit 34 likewise preferably contains at least one separator that separates gases from liquids. The gases are passed into natural gas stream 12. The liquids are passed into crude oil stream 36.

Referring still to FIGS. 2 and 4, blending unit 38 preferably is an apparatus or portion of an apparatus that receives crude 36 and aromatic liquid 26 and mixes them together to produce blended crude 40. In some embodiments, blending unit 38 is a portion of pipe and mixing is achieved by combining the two streams of crude 36 and aromatic liquid 26 together in the pipe. For example a supplemental pipe carrying aromatic liquid 26 may be tied in to a main pipe carrying crude 36. Thus, the portion of pipe may be a section of the main pipe downstream of the tie-in location. Still alternatively, blending unit 38 may be a portion of product separation unit 24. Yet alternatively, it will be understood that blending unit 38 may be any suitable equivalent apparatus or suitable equivalent portion of an apparatus.

Blended crude 40 may then be transported to a refinery or other processing facility. Aromatic hydrocarbons may be separated from blended crude 40 at the refinery or other processing facility. Blended crude 40 has a higher specific gravity than crude 36. Further, blended crude 40 preferably contains a larger volume of liquid than crude 36 and thus the net production of liquid from well fluids 32 is increased. Still further, aromatic liquid 26 preferably contains low sulfur. Thus, addition of aromatic liquid 26 to crude 36 produces a lower sulfur concentration in blended crude 40 than in crude 36.

Referring now to FIGS. 3 and 4, fuel cell 46 may be any conventional fuel cell. Fuel cell 46 preferably generates sufficient power so as to reduce the net external power consumption of systems 42, 44 or other facility power systems.

An integration of separation of associated gas from crude with conversion of the associated gas to aromatics, alternatively to or in combination with generation of power from the hydrogen byproduct of the conversion reaction, provides a combination of advantages of economy.

While the above-described embodiments include a gas processing unit., it will be understood that, depending on the composition of the natural gas, the gas processing unit may be omitted in whole or part.

Non-Oxidative Conversion of Feed Containing Methane to Aromatics

According to a preferred embodiment, non-oxidative conversion of feed stream 16 involves contacting feed stream 16 with a solid catalyst maintained at reaction conditions in non-oxidative conversion zone 18. The term reaction zone will be used herein equivalently with non-oxidative conversion zone. Feed stream 16 preferably contains at least methane. Feed stream 16 can be a stream of essentially pure methane although even a pure stream of gas is likely to contain some small amount that may range from about 0.5 up to 10 mole percent of impurities. The impurities may be nitrogen or other inorganic species. Feed stream 16 can also contains higher hydrocarbons having chain lengths of up to 4, due to the less than perfect separations used in commercial scale processes. Specific examples of such additional hydrocarbons are ethane, propane, n-butane, isobutane, and other compounds as would be known to one of skill in the art. As used herein, it is more preferred that feed stream 16 contains a molar concentration over 40 percent methane, and it is highly preferred that the feed stream contains at least 50 mole percent methane.

One embodiment of the invention comprises the presence of hydrogen in feed stream 16 during the activation of the catalyst. In this embodiment of the invention, it is preferred that the feed stream 16 in the reaction zone 18 contains at least 25 mole percent hydrogen. A highly preferred hydrogen concentration is from about 25 to 75 mole percent. Most preferably, the hydrogen concentration is about 50 mole percent.

In another aspect of the embodiment of the invention, feed stream 16 may contain $C_2$ to $C_4$ alkanes during the activation of the catalyst. More preferably it is ethane, propane, butane or a mixture of two or more of such saturated hydrocarbons. Most preferably it is butane. It is preferred that feed stream 16 for such activation be adjusted to contain at least 50 mole percent hydrogen. A highly preferred hydrogen concentration is from about 50 to 90 mole percent. During such activation, feed stream 16 is brought into contact with the catalyst in a reaction zone at hydrocarbon conversion conditions which include a temperature between about 250° C. and about 800° C., more preferably between about 350° C. and about 550° C. The activation generally takes place at atmospheric pressure, but the pressure may be within the approximate range of about 0.5 bar to 5 bar, more preferably between about 0.5 bar and about 2 bar. The activation is suitably accomplished using a Weight Hourly Space Velocity (WHSV) between about 0.5 h−1 and about 4 $h^{-1}$, and more preferably between about 0.5 and 2 $h^{-1}$.

Feed stream 16 is preferably brought into contact with the catalyst in reaction zone 18. Reaction zone 18 may include a single reactor or several separate reactors in series for the multi-step process. Products $C_6$-plus hydrocarbons for the multi-step process are recovered by means of an intermediate separation step. The catalyst within the reactor is maintained as an immobile or fixed bed. However, processes using one or more fluidized beds could also be operated without detrimental effect on the reaction conversion.

The catalytic composition employed in preferred embodiments of the subject invention may accordingly be characterized as comprising a catalytic composition comprising a crystalline aluminosilicate molecular sieve. This crystalline aluminosilicate eventually having the external surface acidity selectively passivated by means of an amorphous silica layer.

The molecular sieve used in preferred embodiments of the present invention may be a pentasil crystalline aluminosilicate. "Pentasil" is a term used to describe a class of shape-selective molecular sieve. Of the class of pentasil crystalline aluminosilicates, the preferred aluminosilicates are ZSM-5, ZSM-8, ZSM-11, ZSM-23 and ZSM-35, with ZSM-5 being particularly preferred. The ZSM-5 molecular sieve is a coarse crystalline, three-dimensional, stable structure consisting of two sets of intersecting channels through 10-membered ring windows, one straight (5.3×5.6 A) and the other sinusoidal (5.1×5.5 A). This aluminosilicate may be represented by the general formula:

$$M^{n+}{}_{x/n}[(AlO_2)_x(SiO_2)_y]^{x-} \cdot zH_2O$$

where M is a cation that is a positively charged ion selected from a metal ion or an organic ion of valence n or hydrogen, x+y is the total number of tetrahedrals per cell, and z is a function of the degree of hydration and varies from 0 to 16.

Metal cations useful in the formation of ZSM-5 molecular sieves include cetious alkali metals or alkaline earth metals. Because of the basic conditions required for crystallization of the aluminosilicate, the source of such a cation usually is an alkali hydroxide or alkaline earth hydroxide, for example sodium hydroxide. Organic compounds useful in preparing ZSM-5 molecular sieves include alkylammonium cations or precursors such as tetraalkylammonium compounds. Most preferably, it is tetrapropylammonium cations.

The crystalline material can be prepared by mixing a silica source, an alumina source, an alkali metal hydroxide, a nitrogen-containing organic base as template, and water. Preparation of ZSM-5 molecular sieve is described in greater detail in U.S. Pat. No. 3,702,886 and Re. No. 29,948, which are hereby incorporated herein by reference for all purposes.

The preferred ZSM-5 crystalline aluminosilicate used in the preferred embodiments of the present invention has a silica-to-alumina ratio of 50:1.

The methane conversion catalyst used in the aromatization process preferably contains a metal component. The preferred metal component is molybdenum or molybdenum compounds. The final methane conversion catalyst should contain less than 10 wt. percent metal as measured on an elemental analysis basis. It is preferred that the final catalyst contains from about 0.5 to about 4.0 wt. percent total metal component. A highly preferred concentration for molybdenum on the final methane conversion catalyst is from about 0.5 to about 2.0 wt. percent.

Catalytically active metal is deposited onto the crystalline aluminosilicate by means of any of the following methods. The catalytically active metal may be added by the incipient wetness impregnation of a water soluble metal salt, such as the ammonium heptamolybdate. Another suitable method is the direct vaporization of the catalytically active metal, such as molybdenum oxide, onto the crystalline aluminosilicate. Other methods as are known in the art may also be used.

It is preferred that the catalytically active metal is uniformly distributed throughout the entire network of the final methane conversion catalyst rather than merely on the surface of such catalyst.

The crystalline metal-loaded aluminosilicate useful in the aromatization process may preferably be admixed with an amorphous silica matrix depending upon the intended process use. Typically, the surface of the crystalline aluminosilicate is covered with an amorphous silica layer to improve shape selectivity by passivating the external surface of the support which contains acidic sites, coke precursor sites, and non-shape selectivity molybdenum catalyst. The amorphous silica passivating layer has no effect on the accessibility of the pores of the molecular sieve. Amorphous silica layers may be obtained by means of well known techniques as are understood by one skilled in the art. Preferably, said amorphous silica layer is placed on the surface of the crystalline aluminosilicate by means of chemical vapor deposition (CVD) or by means of chemical liquid deposition (CLD) of silicon alkoxides, most preferably tetraethoxysilane. The crystalline aluminosilicate composition that is formed can be separated and recovered by filtration with aqueous washing. Typically, calcination at temperatures ranging from about 350° C. to about 600° C. and preferably from about 450° C. to about 550° C. is necessary to remove organic compounds on the surface of the molecular sieve.

The final methane conversion catalyst can be pelletized and thereafter crushed, and the result sieved to 0.250 to 0.425 mm particles.

Accordingly, in preferred embodiments of the present invention, non-oxidative aromatization of methane may include passing feed stream 16, containing methane, into reaction zone 18 in the presence of the above-described catalyst composition at hydrocarbon conversion conditions which include a temperature between about 600° C. and about 800° C., more preferably between about 675° C. and about 750° C. The reaction generally takes place at atmospheric pressure, but the pressure may be within the approximate range of about 0.5 bar to 5 bar, more preferably between about 0.5 bar and about 2 bar. The reaction is suitably accomplished using a Weight Hourly Space Velocity (WHSV) between about 0.1 and about 10 $h^{-1}$, and more preferable between about 0.1 and 4 $h^{-1}$. A non-oxidative conversion process may produce a reaction zone effluent stream including methane, hydrogen, and a selectivity to aromatic products from $C_6$ to $C_{10}$ of preferably greater than about 30%, more preferably greater than 45%, and most preferably greater than 60%. The hydrogen is preferably passed to hydrogen stream 20. The methane and aromatic products are preferably passed to product stream 22 for separation into gas 28 containing methane and aromatic liquid 26. Exemplary aromatic compounds that may be contained in aromatic liquid 26 include benzene, xylenes, and naphthalene.

In another aspect of a preferred non-oxidatative conversion process, the non-oxidative conversion of a methane-containing gas to aromatic liquid comprises a multi-step process that comprises passing feed stream 16 containing methane, into at least two reactors in series in the presence of the above-described catalyst composition at hydrocarbon conversion conditions, which include a temperature between about 600° C. and about 800° C., more preferably between about 675° C. and about 750° C. The reaction generally takes place at atmospheric pressure, but the pressure may be within the approximate range of about 0.5 bar to 5 bar, more preferably between about 0.5 bar and about 2 bar. The reaction is suitably accomplished using a Weight Hourly Space Velocity (WHSV) between about 0.1 $h^{-1}$ and about 10 $h^{-1}$, and more preferably between about 0.1 $h^{-1}$ and 4 $h^{-1}$. The present process may produce a reaction zone effluent stream that may be divided into product stream 22 including methane and aromatic liquid 26 and hydrogen stream 20, where the aromatic liquids 26 includes products from $C_6$ to $C_{10}$, with at least a selectivity with respect to the reaction zone effluent stream preferably greater than about 30%, more preferably greater than 45%, and most preferably greater than 60%. In a multi-stage system, at least the $C_6$-$C_{10}$ products are preferably recovered in aromatic liquid 26 by means of an intermediate separation step, which results in an intermediate stream that is divided into gas stream 28 containing methane and hydrogen stream 20. Removal of the $C_6$ to $C_{10}$ products in aromatic liquid stream 26 can be accomplished by passing the reaction zone effluent stream through a cold trap or other suitable device. The cold trap lowers the temperature of the reaction zone effluent stream, thereby causing certain products to condense. The intermediate stream is then passed into the next reaction zone in the presence of the above-described catalyst composition. This prevents the catalyst in the next reactor from coke deposition, which is a typical aspect of the non-oxidative conversion process herein described.

In addition to removing the $C_6$ to $C_{10}$ hydrocarbon products between the stages, a preferred system also includes either inter-stage or intra-stage hydrogen removal, or both. In particular, a preferred multi-stage system includes either an organic or norganic hydrogen selective membrane positioned such that hydrogen in the intermediate stream can pass through the membrane and thereby be separated from the remainder of the intermediate stream. Alternatively or in addition, the reactor wall can include or comprise a hydrogen selective membrane, so that hydrogen 20 can be separated from the system continuously during reaction. It will be understood that other hydrogen removal techniques can be applied between the stages or to the reactor systems. Removal of hydrogen 20 from the stream and/or reactor(s) in this manner will drive the reaction toward completion.

In another aspect, one embodiment of the subject process comprises the recycling of the components of the reaction zone 18 from the product recovery facilities. These products may be recycled individually or in admixture. These recycled products 28 could comprise low molecular weight hydrocarbons. For instance, ethane and ethylene recovered from the intermediate separation step may be recycled by admixture into feed stream 16. As another embodiment of the present invention, hydrogen 20 produced in the reaction zone 18, considered also as a valuable product of the process, may be recycled using any of several techniques known to those skilled in the art of hydrocarbon conversion process design. By way of illustration and not limitation, hydrogen 20 may be recovered by the use of membrane separation technology or by the use of adsorptive separation, such as pressure-swing adsorption.

It will be understood that suitable alternative non-oxidative aromatization catalysts, suitable alternative configurations of the reaction zone, and suitable alternative process conditions, are each contemplated singly or in combination, for use with a non-oxidative conversion process according to the preferred embodiments of the present invention.

An advantage of a non-oxidative conversion process is the reduction in power consumption as compared to conversion of natural gas to paraffinic hydrocarbons via the Fischer-Tropsch process due to the lack of necessity for an oxygen generation unit such as an air separation unit.

Should the disclosure of any of the patents and publications that are incorporated herein conflict with the present specification to the extent that it might render a term unclear, the present specification shall take precedence.

While preferred embodiments of this invention have been shown and described, modifications thereof can be made by one skilled in the art without departing from the spirit or teaching of this invention. The embodiments described herein are exemplary only and are not limiting. Many variations and modifications of the method are possible and are within the scope of the invention. Accordingly, the scope of protection is not limited to the embodiments described herein, but is only limited by the claims that follow, the scope of which shall include all equivalents of the subject matter of the claims.

We claim:

1. A process for converting a gaseous hydrocarbon stream to an aromatic hydrocarbon stream, comprising:
    (a) passing the gaseous stream from a wellhead to a non-oxidative conversion zone proximal to the wellhead; and
    (b) contacting the gaseous stream with a catalyst so as to produce the aromatic liquid stream, wherein the catalyst is contained in the conversion zone.

2. The process according to claim 1 wherein the production of the aromatic liquid stream proceeds directly from the gaseous stream, without intermediate reaction.

3. The process according to claim 1 wherein the gaseous stream comprises at least 40 volume % methane.

4. The process according to claim 1 wherein the gaseous stream comprises at least 50% volume methane.

5. The process according to claim 1 wherein the aromatic stream comprises aromatic hydrocarbons selected from the group consisting of benzene, xylenes, and naphthalene.

6. The process according to claim 1 wherein the conversion zone is located onshore.

7. The process according to claim 1 wherein the conversion zone is located on an offshore facility.

8. The process according to claim 7 wherein the offshore facility comprises a fixed platform.

9. The process according to claim 7 wherein the offshore facility comprises a floating structure.

10. The process according to claim 1 further comprising:
    (c) passing byproduct hydrogen produced from contact of the gaseous stream with the catalyst to a power generation unit.

11. The process according to claim 10 wherein the power generation unit comprises a fuel cell.

12. The process according to claim 10 wherein the power generation unit comprises a combustion chamber adapted for combustion of hydrogen.

13. The process according to claim 10 further comprising:
    (d) passing power from the power generation unit to a power consuming unit.

14. The process according to claim 13 wherein the power consuming unit comprises the conversion zone.

15. The process according to claim 13 wherein the conversion zone is located on an offshore facility.

16. The process according to claim 15 wherein the power consuming unit comprises the facility.

17. The process according to claim 16 wherein the facility comprises a floating structure.

18. The process according to claim 15 wherein the power consuming unit comprises a system located on or within the facility.

19. A process for converting wellhead fluids to blended crude, comprising:
    (a) separating the fluids into associated gas and crude oil;
    (b) passing a methane-containing feed stream derived from the associated gas to a non-oxidative conversion zone so as to produce an aromatic liquid;
    (c) blending the aromatic liquid with the crude oil so as to produce the blended crude; and
    wherein steps (a) through (c) are carried out proximal to the wellhead.

20. The process according to claim 19 wherein the feed stream comprises at least 40 volume % methane.

21. The process according to claim 19 wherein the feed stream comprises at least 50% volume methane.

22. The process according to claim 19 wherein the aromatic liquid comprises aromatic hydrocarbons selected from the group consisting of benzene, xylenes, and naphthalene.

23. The process according to claim 19 wherein the conversion zone is located onshore.

24. The process according to claim 19 wherein the conversion zone is located on an offshore facility.

25. The process according to claim 24 wherein the offshore facility comprises a fixed platform.

26. The process according to claim 24 wherein the offshore facility comprises a floating structure.

27. The process according to claim 19 further comprising:
   (d) passing byproduct hydrogen produced from contact of the gaseous stream with the catalyst to a power generation unit.

28. The process according to claim 27 wherein the power generation unit comprises a fuel cell.

29. The process according to claim 27 wherein the power generation unit comprises a combustion chamber adapted for combustion of hydrogen.

30. The process according to claim 27 further comprising:
   (e) passing power from the power generation unit to a power consuming unit.

31. The process according to claim 30 wherein the power consuming unit comprises the conversion zone.

32. The process according to claim 30 wherein the conversion zone is located on an offshore facility.

33. The process according to claim 32 wherein the power consuming unit comprises the facility.

34. The process according to claim 32 wherein the facility comprises a floating structure.

35. The process according to claim 32 wherein the power consuming unit comprises a system located on or within the facility.

36. A process for delivering a blended crude to a destination comprising:
   (a) separating wellhead fluids into associated gas and crude oil;
   (b) passing a methane-containing feed stream derived from the associated gas to a non-oxidative conversion zone so as to produce an aromatic liquid;
   (c) blending the aromatic liquid with the crude oil so as to produce the blended crude;
   (d) transporting the blended crude to the destination; and
   wherein steps (a) through (c) are carried out proximal to the wellhead.

37. The process according to claim 36 wherein the blended crude is transported by a pipeline.

38. The process according to claim 36 wherein the blended crude is transported by shuttle tanker.

* * * * *

UNITED STATES PATENT AND TRADEMARK OFFICE
CERTIFICATE OF CORRECTION

PATENT NO. : 7,019,184 B2 Page 1 of 1
APPLICATION NO. : 10/139502
DATED : March 28, 2006
INVENTOR(S) : Joe D. Allison et al.

It is certified that error appears in the above-identified patent and that said Letters Patent is hereby corrected as shown below:

Cover Page, item [75,] after "Neil Meldrum" delete "Houston, TX" and insert --Aberdeen, Scotland--. after "Doug S. Jack" delete "Ponca City, OK" and insert --Houston, TX--.

Cover Page, Sec. 73, after Assignee, delete "Conocophillips" and insert --ConocoPhillips--.

Cover Page, Abstract, line 6, delete "welihead" and insert --wellhead--.

Column 2, line 59, after "located" insert --on--.

Column 4, line 5, after "contains" delete "26".

Column 4, line 5, after "liquid" insert --26--.

Column 5, line 67, after "unit" delete ".".

Column 6, line 16, delete "contains" and insert --contain--.

Column 10, line 56, delete "welihead" and insert --wellhead--.

Signed and Sealed this

Fifteenth Day of May, 2007

JON W. DUDAS
*Director of the United States Patent and Trademark Office*